United States Patent [19]

Cornelius

[11] 4,212,863

[45] Jul. 15, 1980

[54] HIGHLY CONCENTRATED PHARMACEUTICAL FORMULATIONS OF STEROIDS AND PROCESSES FOR THEIR PREPARATION

[75] Inventor: Lammert Cornelius, Boxmeer, Netherlands

[73] Assignee: Akzo N.V., Arnhem, Netherlands

[21] Appl. No.: 953,877

[22] Filed: Oct. 23, 1978

[30] Foreign Application Priority Data

Oct. 29, 1977 [NL] Netherlands .......................... 7711916

[51] Int. Cl.$^2$ ............................................. A61K 31/56
[52] U.S. Cl. ..................................................... 424/240
[58] Field of Search ................................ 424/240, 284

[56] References Cited

U.S. PATENT DOCUMENTS

| | | | |
|---|---|---|---|
| 2,791,609 | 5/1957 | Kaplan ................................. | 424/240 |
| 3,025,311 | 3/1962 | Gutsell, Jr. et al. ................. | 424/240 |
| 3,085,939 | 4/1963 | Wruble et al. ....................... | 424/240 |
| 3,149,037 | 9/1974 | Aiello et al. ......................... | 167/81 |
| 3,636,195 | 1/1972 | Monson ............................... | 424/240 |

FOREIGN PATENT DOCUMENTS 2240187 2/1974 Fed. Rep. of Germany .
1081667 4/1966 United Kingdom .
1453239 10/1976 United Kingdom .

OTHER PUBLICATIONS

Chemical Abstracts, vol. 82, No. 4 (1975) Paragraph 21, 826(g).

*Primary Examiner*—Elbert L. Roberts
*Attorney, Agent, or Firm*—Stevens, Davis, Miller & Mosher

[57] ABSTRACT

The invention relates to highly concentrated liquid pharmaceutical formulations of steroids of the oestrane, androstane and (19-nor-)pregnane series comprising tocol or a derivative thereof that is fluid at normal temperature, or mixtures thereof, in an amount of at least 10% by weight of the formulation, and optionally one or more of the usual fluid carriers, such as vegetable oil, benzyl benzoate and/or benzyl alcohol.

10 Claims, No Drawings

HIGHLY CONCENTRATED PHARMACEUTICAL FORMULATIONS OF STEROIDS AND PROCESSES FOR THEIR PREPARATION

The invention relates to highly concentrated pharmaceutical formulations of steroids of the oestrane, androstane and (19-nor-)pregnane series, the said formulations being fluid at normal temperature, and to processes for their preparation.

Injection preparations of steroids are known. Such preparations usually consist of solutions of the steroids in oily carriers, such as arachis oil, sesame oil, olive oil and similar carriers, to which yet other excipients may, if desired, be added, such as benzyl alcohol and benzyl benzoate. Such fluid preparations may be injected almost without damage to tissues, and absorption of the active substance by the organism takes place from the subcutaneous or intramuscular depot thus obtained. The extent and the duration of the absorption depends on various factors including the dosage and concentration of the steroid and the physical properties of the steroid, such as lipophilicity. The upper limit of the concentration is naturally governed by the solubility of the steroid in the carrier. If this solubility is not very great, achievement of the desired effect will necessitate repeating injections at shorter intervals or injecting larger volumes, and there are of course objections to both of these procedures.

It is known that the solubility of steroids in vegetable or animal oils can be increased by the addition of excipients such as benzyl alcohol and benzyl benzoate. An objection to the use of such excipients, and specifically benzyl alcohol in somewhat higher concentration, is that these agents may irritate the tissues.

Other ways of administration to give higher concentrations in the subcutaneous or intramuscular depot are the injection of crystal suspensions or the implantation of solid formulations. The preparation of stable crystal suspensions may give rise to problems, while the surgical intervention, though minor, constitutes an objection to the implantation.

When the preparation and use of a highly concentrated long-acting injection preparation of steroids is therefore desired, for example an injection preparation for the inhibition of ovulation in animals or man, one or more of the above-noted objections will be valid to a greater or lesser extent.

The administration of steroids in solution, for example a solution in oil, by the oral route is also known; see for example the Dutch Patent Application No. 7402689.(=British Pat. No. 1,500,374).

The administration of fluid pharmaceutical preparations by the oral route may be realized in various ways. The prescribed quantity, for example a number of drops or ml, may be taken per spoon, on a sugar lump or together with food. The solution may also be taken "sealed" in a soft gelatine capsule or in microcapsules.

With the oral administration of certain steroids in solution, for example testosterone and esters thereof, the problem may also arise that the solubility (and therefore the amount of active agent per dosage unit) in the known solvents is relatively low, so that either more or larger dosage units must be administered on each occasion or the administration of the preparation must be repeated at shorter intervals. There are objections to both procedures. In such cases there is an obvious need for solutions with greater concentrations.

It has now surprisingly been found that highly concentrated formulations of steroids, said formulations being fluid at normal temperature, and said steroids being of the oestrane, androstane and (19-nor-)pregnane series, may be prepared by dissolving the steroids in tocol or in a derivative thereof which is liquid at normal temperature (15°–30° C.), or in a mixture of two or more of these derivatives whereby the quantity of tocol or derivative thereof in the formulation is at least 10% by weight.

Hence, the invention relates to the highly concentrated steroid formulations thus obtained, and to the processes for their preparation.

Tocol and the derivatives liquid at normal temperature may be represented by the general formula:

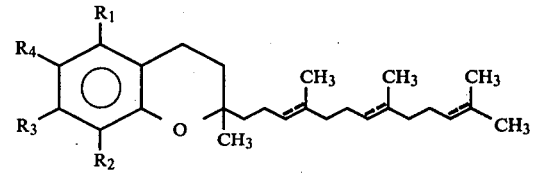

where
$R_1$=H, $CH_3$ or $C_2H_5$;
$R_2$=H, $CH_3$ or $C_2H_5$;
$R_3$=H, $CH_3$ or $C_2H_5$;
$R_4$=H, OH, O-acyl (1-2 atoms) or O-alkyl (1-2 C-atoms); and
the dotted lines denote the optional presence of a carbon-carbon double bond.

The compounds in which the side-chain in the formula given above contain one or two isoprene residues

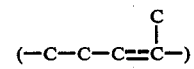

less than indicated are also included amongst the tocol derivatives noted above.

For tocol itself, $R_1=R_2=R_3$=H, $R_4$=OH and the side-chain is saturated. Examples of tocol derivatives are: 5-methyltocol, 7-methyltocol, 8-methyltocol, 5,7-dimethyltocol, 5,8-dimethyltocol, 7,8-dimethyltocol, 5,7,8-trimethyltocol, 8-methyltocotrienol, 7,8-dimethyltocotrienol, 5,8-dimethyltocotrienol, 5,7,8-trimethyltocotrienol, 5,7-di-ethyltocol, 5,7-dimethyl-8-ethyltocol, 5,7-di-ethyl-8-methyltocol, the formates and acetates, as well as the methyl and ethyl esters of these compounds, and 6-desoxytocol. Use is preferably made of tocol, 5,7,8-trimethyltocol(α-tocopherol) or 8-methyltocol(δ-tocopherol). In practice use is generally made of the racemates dl-tocol, dl-α-tocopherol and dl-δ-tocopherol.

During the preparation of a formulation according to the invention, excipients such as benzyl alcohol or benzyl benzoate may optionally also be used, or a quantity of an oily carrier such as arachis oil or sesame oil may be added. Such a use or addition may be desirable in the preparation of injection formulations in order to lower the viscosity and in this way make the preparation easier to inject; in other words, to enable the formulation to be injected through a needle of the desired bore.

The amount of tocol or derivative thereof in the preparation is preferably at least 25% w/w, which means that at least 100 mg and preferably 250 mg tocol or derivative thereof is present in a milliliter (about 1000 mg) of solution. The upper limit of the quantity of tocol or derivative thereof is of course determined by the amount of steroid which can be dissolved in the carrier, and depends to some extent on both the steroid and the carrier; it lies between 50 and 90% w/w and is generally between 60 and 80% w/w. This means that the maximum amount of steroid per ml solution (about 1000 mg), again depending on the steroid and the carrier, will be between 100 and 500 mg and generally may be 200–400 mg.

The process offers particular advantages for steroids of the oestrane, androstane and (19-nor-) pregnane series containing at least a 3-oxo-$\Delta^4$-group and an optionally esterified hydroxy group at position 17 and/or 21 (if present), since with these steroids much higher concentrations can be achieved than is possible with the known solvents and concentrations of 100 to 400 mg in the absolute sense are furthermore possible; for certain steroids with the characteristics noted, even concentrations up to 500 mg per ml tocol or derivative thereof are possible.

Examples of oestrane, androstane and (19-nor-) pregnane compounds with at least a 3-oxo-$\Delta^4$-group and an optionally esterified hydroxy group at position 17 and/or 21 (when present) are: testosterone, 19-nor-testosterone (nandrolone), progesterone, 19-nor-progesterone, 17α-hydroxyprogesterone, 17α-hydroxy-19-nor-progesterone, 21-hydroxy-progesterone, 21-hydroxy-19-nor-progesterone, 16α-ethyl-21-hydroxy-progesterone, 16α-ethyl-21-hydroxy-19-nor-progesterone, 16-methylene-17α-hydroxy-progesterone, corticosterone, desoxycorticosterone, cortisone, hydrocortisone, prednisolone, aldosterone and the 17 and/or 21 esters of these steroids derived from organic mono- or di-carboxylic acids with 1 or 2, respectively, to 18 carbon atoms.

Examples of such organic mono- and di- carboxylic acids are aliphatic carboxylic acids such as propionic acid, butyric acid, isocaproic acid, decanoic acid, α-methyldecanoic acid, lauric acid, myristic acid, oleic acid, palmitic acid, trimethylacetic acid, undecenoic acid, malonic acid, succinic acid, glutaric acid and tartaric acid, cyclo-aliphatic carboxylic acids, such as cyclohexane-carboxylic acid, cyclopentylpropionic acid and cyclohexylbutyric acid, araliphatic carboxylic acids such as phenylacetic acid and phenylpropionic acid, and aromatic carboxylic acids such as benzoic acid.

The steroids named may also be further substituted at positions 6, 7 and/or 11, for example by a methyl, ethyl or methylene group, and/or may contain a further double bond, for example a $\Delta^6$ bond.

The preparations obtained according to the invention, depending on the steroid present, may be used for various indications. Preparations based on testosterone and esters thereof may be used as androgenically active preparations in substitution therapy. Preparations based on oestrogens may be used in cases of oestrogen deficiency. Preparations containing nandrolone or esters thereof can find use as anabolic preparations or ovulation-inhibiting preparations. Preparations based on progesterone or progesterone derivatives may be used as progestagenic preparations, not only for the maintenance of a pregnancy but also for prevention of pregnancy (ovulation inhibiting action) and they may furthermore be used for the treatment of endometrial carcinoma. For use as ovulation inhibitors, long-acting esters of 17α-hydroxy-progesterone, such as for example, 17α-hydroxy-progesterone caproate and medroxy-progesterone acetate, are used. Preparations containing corticosteroids may be used in those cases in which mineralocorticoid, glucocorticoid, anti-inflammatory, anti-allergic, anti-shock or analgesic activity is desired.

An interesting application of those preparations according to the invention based on nandrolone esters, in particular nandrolone esters derived from organic carboxylic acids with more than 7 carbon atoms, for example nandrolone phenylpropionate, is the use as an injection preparation for the regulation of oestrus in animals. Such an injection preparation offers particular advantages for the suppression of oestrus in domestic animals such as dogs. Since it is possible, in accordance with the invention, to prepare injection formulations containing well over 300 mg nandrolone ester, for example nandrolone palmitate, per ml, it is possible to suppress oestrus in dogs for more than 3 months with a single injection of 1 ml. Only concentrations of 50 to 100 mg per ml can be obtained with the known solvents such as arachis oil, while the addition of benzyl benzoate and/or benzyl alcohol enables concentrations of 100 to 200 mg per ml to be reached with certain nandrolone esters, for example nandrolone palmitate. For the suppression of oestrus, therefore, either a larger volume (2 to 5 ml) would have to be injected, or the injection would have to be repeated at an earlier date, and there are objections to both these procedures.

On using injection preparations according to the invention based on nandrolone esters for the suppression of oestrus in animals it was furthermore shown that, specifically with the preparations based on nandrolone esters derived from aliphatic carboxylic acids with 9–18 carbon atoms, an additional depot effect (prolonged activity or sustained release effect) appears, so that the very high concentration in the depot, particularly during the initial phase, does not result in an undesirably high blood level; unwanted side-effects as a result of excessively high blood levels do not therefore occur.

Another interesting use of the preparations according to the invention is the oral administration in the form of soft gelatine capsules containing a highly concentrated solution of the steroids in tocol or a derivative thereof. This use is specifically of importance for the oral administration of testosterone and nandrolone, in particular the esters of these steroids derived from organic carboxylic acids.

The activity of both testosterone and nandrolone is much lower on oral administration than on parenteral administration. It is true that this difference proves to be smaller for the esters of these compounds, but it may nevertheless still constitute an adequate reason for choosing the parenteral administration form in preference to the oral form, particularly in those cases where the doses to be administered are relatively high, as, for example, in androgen substitution therapy, and a large number of dosage units or a relatively large dosage unit (swallowing problem!) have or has, respectively, to be given on each occasion or alternatively the dosage has to be repeated at shorter intervals. In such cases, use of the highly concentrated solutions according to the invention can weigh the scales in favour of the medically and technically easier oral dosage form, such as the soft gelatine capsule containing the concentrated solution of, for example, a testosterone or nandrolone ester. Such an oral administration form furthermore offers the advantage that the active agent is made available to the organism in a lipoid solution, which has a favourable effect on the activity of the preparation. In this connection see the Belgian Patent Specifications Numbers 826086 and 845613.

It is known that certain tocol derivatives possess vitamin E activity. For many applications, such as suppression of oestrus in animals, this is not objectionable, but for applications in the human sector the vitamin E activity of a preparation according to the invention may be a drawback. It is however known that the various tocols possess differing vitamin E activities, and that tocol itself and certain derivatives, for example 5,7-diethyltocol and 6-desoxytocol, possess little or no vitamin E activity, so that a formulation with the desired low vitamin E activity or a formulation devoid of vitamin E activity can be prepared according to the choice of carrier.

The invention is illustrated by means of the following examples.

EXAMPLE I

Saturated solutions of a number of steroids in 5,7,8-trimethyltocol (α-tocopherol) were prepared at 21° C. The concentration of steroid in mg per ml solution is given in column a of Table A. Column b gives the concentration of steroid in mg per ml in a saturated solution in a solvent comprising equal parts by volume of α-tocopherol and arachis oil, while for comparison column c shows the concentration of steroid in mg per ml in a standard solution in arachis oil.

Table A

| Steroid | a | 6 | c |
|---|---|---|---|
| testosterone | 100 | 40 | 5 |
| corticosterone | 40 | 2 | 1 |
| 16α-ethyl-21-hydroxy-progesterone-21-decanoate | 500 | 200 | 50 |
| 16α-ethyl-21-hydroxy-progesterone-21-heptanoate | >225 | >225 | 140 |
| dinandrolone oxydiacetate | 120 | 20 | 10 |
| dinandrolone adipate | 180 | 85 | 2 |
| testosterone undecanoate | >225 | >225 | 85 |
| nandrolone palmitate | 400 | 200 | 75 |

EXAMPLE II 300 g nandrolone palmitate and 250 g α-tocopherol were added to a mixture of 100 g benzyl alcohol and 250 g benzyl benzoate which had been warmed to 70° C. After stirring for a while, a clear solution was obtained. The solution was cooled to room temperature after which the volume was adjusted to 1000 ml by addition, with stirring, of arachis oil (about 100 g). The solution thus obtained was filled into 1000 vials in a volume of 1 ml solution each, after which the vials were closed with oil-resistant rubber stoppers and so-called open "Ciliatto" capsules. The vials were finally heated at 121° C. for 30 minutes in an autoclave.

In a similar way, but using tocol instead of α-tocopherol, and in another batch δ-tocopherol instead of α-tocopherol, solutions were prepared and vials were filled with 1 ml solution containing 300 mg nandrolone palmitate.

The injection preparations thus obtained proved to be eminently suitable for use in the suppression of oestrus in dogs, a single injection of 1 ml made using a syringe fitted with a 19 G needle giving suppression of oestrus lasting at least 3 months.

EXAMPLE III

A sterile solution of testosterone undecanoate in tocol, containing 208.35 g per liter, was made. In the way usual in the pharmaceutical technique, this solution was encapsulated under aseptic conditions in soft gelatine capsules with a volume (contents) of 0.24 ml, so that the testosterone undecanoate content was 50 mg per capsule. The capsule wall (113 mg) consisted of gelatine (77 mg), glycerine (17.5 mg), sorbitol (15.5 mg), parabens (0.5 mg), TiO$_2$ (0.6 mg) and Cochineal Red A (1.9 mg; dye).

A number of other steroids were dissolved in tocol and encapsulated in soft gelatine capsules in a similar way. Details are given in Table B.

Table B

| Steroid | Capsule content (ml) | mg steroid per capsule |
|---|---|---|
| Testosterone α-methyldecanoate | 0.12 | 25 |
| Nandrolone decanoate | 0.18 | 50 |
| Nandrolone α-methyl-β-cyclohexylpropionate | 0.08 | 20 |
| Dinandrolone oxydiacetate | 0.24 | 25 |

EXAMPLE IV

Injection formulations of a number of steroids in a solution based on tocol, benzyl alcohol, benzyl benzoate and arachis oil (50:5:20:25) were prepared in the usual way (see Example II) and filled into 1 ml capsules. The steroids are given in Table C, together with their concentrations in mg per ml solution.

Table C

| Steroid | mg per ml |
|---|---|
| Nandrolone phenylpropionate | 200 |
| 16α-ethyl-21-hydroxyprogesterone-21-decanoate | 350 |
| Dinandrolone oxydiacetate | 75 |
| Oestradiol phenylpropionate | 50 |
| 17α-hydroxyprogesterone caproate | 150 |
| Nandrolone palmitate/laurate (2:1) | 300 |

I claim:

1. A highly concentrated liquid pharmaceutical steroid formulation comprising (1) at least one steroid of the oestrane, androstane or (19-nor-)pregnane series containing at least a 3-oxo-Δ$^4$-group and an hydroxy group at position 17 and or 21 (if present) and (2) a solvent for said steroid comprising at least one of tocol or a derivative thereof that is fluid at normal temperatures and of the formula:

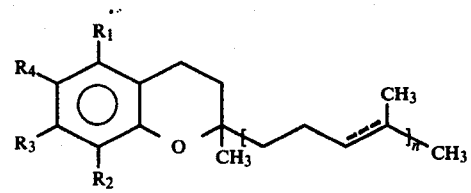

where
R$_1$=H, CH$_3$, or C$_2$H$_5$;
R$_2$=H, CH$_3$, or C$_2$H$_5$;
R$_3$=H, CH$_3$, or C$_2$H$_5$;
R$_4$=H, OH, O-C$_{1-2}$ acyl, OCH$_3$, or C$_2$H$_5$; and
n=1, 2, or 3;
the dotted lines indicate the optional presence of a carbon atom double bond, with the proviso that said tocol or derivative constitutes at least 10% by weight of said formulation.

2. The formulation of claim 1, wherein said tocol or derivative thereof is selected from the group consisting of tocol, α-tocopherol and δ-tocopherol.

3. The formulation of claims 1 or 2, wherein said tocol or derivative thereof constitutes at least 25% by weight of said formulation.

4. The steroid formulation of claim 1 where the hydroxy group of the steroid is esterified.

5. The steroid formulation of claim 1 further containing at least one fluid carrier selected from the group consisting of vegetable oils, benzyl benzoate, and benzyl alcohol with the proviso that said tocol or derivative constitutes at least 10% by weight of said formulation.

6. A process for preparing a highly concentrated pharmaceutical steroid formulation comprising dissolving at least one steroid of the oestrane, androstane, or (19-nor-) pregnane series containing at least a 3-oxo-Δ⁴-group and an hydroxy group at position 17 and or 21 (if present) in at least one of tocol or a derivative thereof that is liquid at normal temperatures and of the formula:

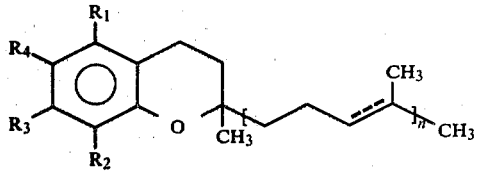

where
$R_1$=H, $CH_3$, or $C_2H_5$;
$R_2$=H, $CH_3$, or $C_2H_5$;
$R_3$=H, $CH_3$, or $C_2H_5$;
$R_4$=H, OH, O-$C_{1-2}$ acyl, or $C_2H_5$; and
n=1, 2, or 3;
the dotted lines indicate the optional presence of a carbon atom double bond, with the proviso that said tocol or derivative constitutes at least 10% by weight of said formulation.

7. Process according to claim 6, characterized in that said tocol or derivative thereof is selected from the group consisting of tocol, α-tocopherol and γ-tocopherol.

8. The process of claim 6 wherein the hydroxy group of the steroid is esterified.

9. The process of claim 6 comprising further adding at least one fluid carrier selected from the group consisting of vegetable oils, benzyl benzoate, and benzyl alcohol to the formulation with the proviso that said tocol or derivative constitutes at least 10% by weight of said formulation.

10. Process according to claims 6, 7, 8 or 9, characterized in that said tocol or derivative thereof constitutes at least 25% by weight of said formulation.

* * * * *

UNITED STATES PATENT AND TRADEMARK OFFICE
CERTIFICATE OF CORRECTION

PATENT NO. : 4,212,863
DATED : July 15, 1980
INVENTOR(S) : Lammert CORNELIUS

It is certified that error appears in the above-identified patent and that said Letters Patent are hereby corrected as shown below:

Line 3 of the Abstract, change "comprising" to --containing--.

Column 2, line 51, change "esters" to --ethers--.

Column 6, line 63, in claim 1, change "$C_2H_5$" to read --$OC_2H_5$--.

Column 8, line 14, in claim 6, change "or $C_2H_5$" to read --$OCH_3$ or $C_2H_5$--.

Signed and Sealed this

Fourth Day of May 1982

[SEAL]

Attest:

GERALD J. MOSSINGHOFF

Attesting Officer    Commissioner of Patents and Trademarks

UNITED STATES PATENT AND TRADEMARK OFFICE
CERTIFICATE OF CORRECTION

PATENT NO. : 4,212,863
DATED : July 15, 1980
INVENTOR(S) : Lammert CORNELIUS

It is certified that error appears in the above-identified patent and that said Letters Patent are hereby corrected as shown below:

Column 8, line 14, in claim 6, change "$OCH_3$ or $C_2H_5$" to read --$OCH_3$ or $OC_2H_5$--.

Signed and Sealed this

Twentieth Day of July 1982

[SEAL]

Attest:

Attesting Officer

GERALD J. MOSSINGHOFF

Commissioner of Patents and Trademarks